United States Patent [19]
Doyle

[11] Patent Number: 5,863,198
[45] Date of Patent: Jan. 26, 1999

[54] ORTHODONTIC BRACKET PLACEMENT JIG

[76] Inventor: Walter A. Doyle, 1088 Nicklaus Ct., Lexington, Ky. 40511

[21] Appl. No.: 717,848

[22] Filed: Sep. 23, 1996

[51] Int. Cl.⁶ ..................................................... A61C 7/00
[52] U.S. Cl. ................................................................. 433/3
[58] Field of Search ................................... 433/2, 3, 8, 24

[56] References Cited

U.S. PATENT DOCUMENTS

| | | | |
|---|---|---|---|
| 4,183,141 | 1/1980 | Dellinger et al. | 433/24 |
| 4,284,405 | 8/1981 | Dellinger | 433/24 |
| 4,523,908 | 6/1985 | Drisaldi et al. | 433/8 |
| 4,526,540 | 7/1985 | Dellinger | 433/24 |
| 4,551,096 | 11/1985 | Dellinger | 433/24 |
| 4,626,208 | 12/1986 | Hall | 433/3 |
| 4,657,508 | 4/1987 | Dellinger | 433/24 |
| 5,011,405 | 4/1991 | Lemchen | 433/24 |
| 5,139,419 | 8/1992 | Andreiko et al. | 433/24 |
| 5,238,402 | 8/1993 | Rohlcke et al. | 433/2 |
| 5,368,478 | 11/1994 | Andreiko et al. | 433/24 |
| 5,395,238 | 3/1995 | Andreiko et al. | 433/24 |
| 5,439,378 | 8/1995 | Damon | 433/8 |
| 5,586,881 | 12/1996 | Chikami | 433/3 |

*Primary Examiner*—Cary E. O'Connor
*Attorney, Agent, or Firm*—Emrich & Dithmar

[57] ABSTRACT

A positioning fixture, or jig, adapted for use with conventional, off-the-shelf orthodontic appliance brackets and arch wires is shaped for optimum placement of the bracket on its associated tooth. Computer modeling of each tooth using digital scanning techniques allows each jig to be custom sized and shaped by CAD/CAM. The jig may be translucent for use with a light sensitive adhesive applied to the bracket to permit light curing of the adhesive. The jig may further be provided with one or more color-coded indicia such as for designating the arch and the particular tooth with which the jig is to be used. The jig may be further provided with elasticity to allow for deformation or failure of the jig to facilitate its removal and may also include an integral occlusal standoff extension to ensure proper in/out, or prominence, registration from the tooth's enamel surface as well as an alignment tab to ensure proper positioning of the jig on its associated tooth. The width of the jig may vary from the width of the appliance to the full width of the tooth itself, where the tooth lacks distinguishing anatomy. A set of jigs for a full set of teeth is packaged in a blister pack arrangement, with each jig attached to an associated removable brace for secure, fixed positioning within an individual upraised compartment of the blister pack. The jig may also span a gap between adjacent teeth for attaching an orthodontic bracket to one of the teeth where sufficient stabilization of the jig cannot be achieved by engaging the target tooth alone.

17 Claims, 3 Drawing Sheets

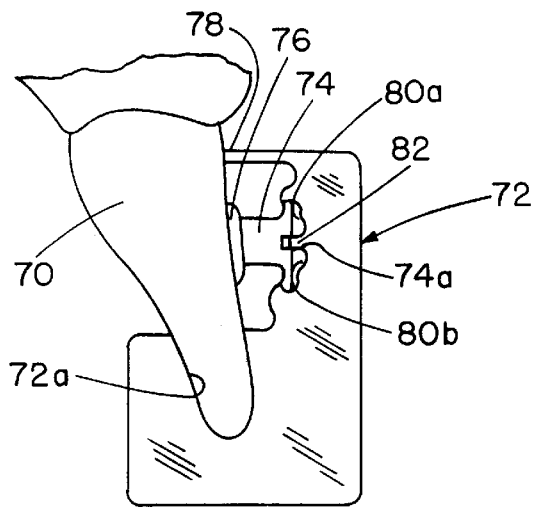
FIG. 5
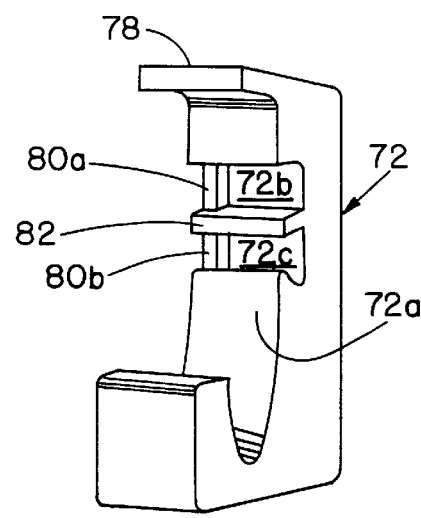
FIG. 6
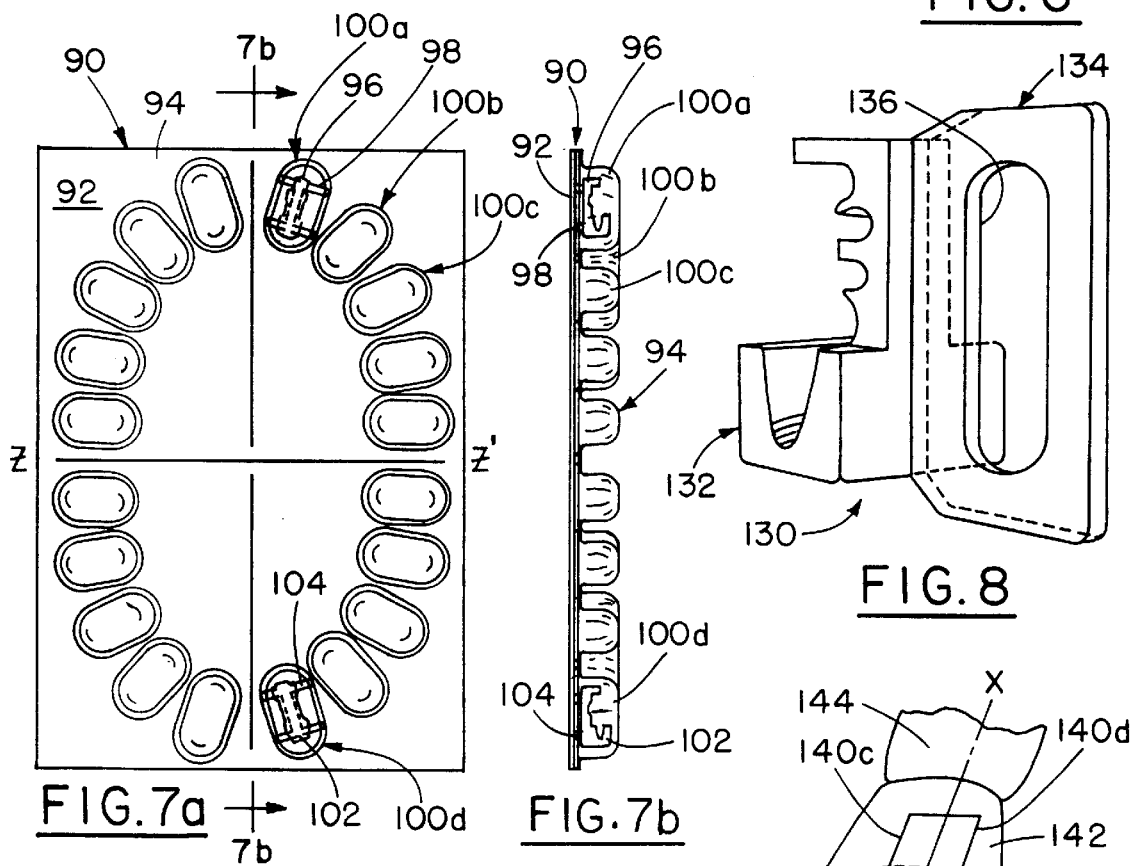
FIG. 7a  FIG. 7b  FIG. 8
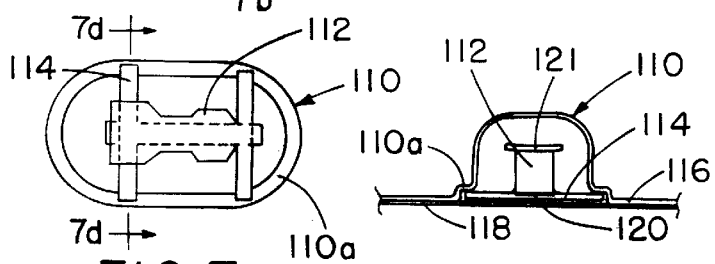
FIG. 7c  FIG. 7d
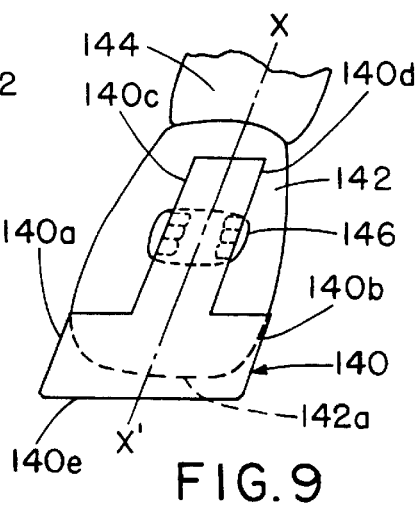
FIG. 9

ORTHODONTIC BRACKET PLACEMENT JIG

FIELD OF THE INVENTION

This invention relates generally to orthodontic appliances and is particularly directed to a jig for attaching an orthodontic bracket to a tooth and an installation method therefor.

BACKGROUND OF THE INVENTION

Orthodontic braces comprised of a plurality of brackets and an arch wire for applying the appropriate force to a patient's teeth are commonly used to move the teeth into a desired configuration or alignment. Each bracket is firmly attached to its associated tooth and serves as a handle on the tooth for the force-producing arch wire. Early approaches provided control of the magnitude and direction of the orthodontic forces by incorporating appropriate bends in the arch wire. Later approaches employed a "straight wire", where the force vector directions were transferred from the arch wire to the individual brackets. This is accomplished by incorporating an arch wire-receiving slot in each bracket so that the desired force is applied to each tooth in the arch by simply attaching a straight length of wire having a rectangular cross section into the slot of each bracket. In a typical straight wire system, the bracket force vectors for specific tooth types are determined so as to match population averages. There is no individual adaptability for the specific needs of an individual patient. The patient's individual pretreatment malocclusion, dental morphology, and facial parameters do not enter into the specific treatment employed. If the bracket is not correctly positioned on the tooth, the desired displacement and/or reorientation of the tooth will not be realized.

Later approaches have employed orthodontic appliance placement methods which take into consideration the individual parameters of the patient. For example, U.S. Pat. No. 5,139,419 discloses a method of forming an orthodontic brace involving calculations based upon measurements of the patient's teeth for determining the positions, angles and depths of the arch wire-engaging grooves in the individual brackets of the appliance. A similar approach is disclosed in U.S. Pat. No. 5,395,238 which employs a mechanical probe of determining the contours of a patient's teeth. U.S. Pat. No. 5,011,405 discloses a method for determining orthodontic bracket placement involving the generation of digital information defining the shape and location of the maloccluded tooth in the patient's jaw, from which digital information a mathematical model of the tooth and jaw is generated for calculating the correct placement position of a bracket on the tooth. U.S. Pat. No. 4,551,096 discloses an apparatus and method for treating malocclusion involving the use of a fixture which fits over a tooth on which a bracket is to be affixed, where the shape and dimensions of the fixture match the shape and contour of a portion of the associated tooth. All of the aforementioned approaches employ a standard fixture, or jig, for positioning of the bracket on its associated tooth. The use of an off-the-shelf jig limits the accuracy with which the bracket can be positioned on the tooth as well as the precision with which the tooth can be aligned in the desired position and orientation.

The present invention addresses the aforementioned limitations of the prior art by providing a custom-shaped positioning jig for attaching an orthodontic appliance bracket to a tooth in installing orthodontic braces. The shape and configuration of the inventive positioning jig is determined using CAD/CAM techniques and the jig is provided with various features which facilitate its use, as well as its installation on and removal from a patient's teeth.

OBJECTS AND SUMMARY OF THE INVENTION

Accordingly, it is an object of the present invention to provide an improved jig for attaching a conventional orthodontic bracket to a tooth.

It is another object of the present invention to provide a custom designed jig for more precise and accurate positioning of an orthodontic bracket and brace combination on a patient's teeth.

Yet another object of the present invention is to provide an improved orthodontic jig which includes various structural features which facilitate installation of the jig on, and attachment of an associated bracket to, a tooth and removal of the jig from the tooth.

A further object of the present invention is to provide an improved packaging arrangement for a set of orthodontic jigs used for installing an arch wire brace arrangement.

This invention contemplates apparatus for attaching an orthodontic bracket to a tooth of a patient by means of an adhesive, the apparatus comprising: a housing; a first recessed portion of the housing for receiving and engaging the tooth in a tight-fitting manner; a second recessed portion of the housing for receiving and engaging the orthodontic bracket and for securely maintaining the orthodontic bracket in contact with an adhesive on a lateral surface of the tooth; and a color-coded feature of the housing for indicating the location in the patient's mouth where the apparatus is to be installed.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

FIG. 5 is a side elevation view of another embodiment of a jig for attaching an orthodontic bracket to a tooth in accordance with the present invention;

FIG. 6 is a perspective view of the jig shown in FIG. 5;

FIG. 7a is a plan view of an orthodontic jig packaging arrangement in accordance with yet another aspect of the present invention;

FIG. 7b is a sectional view of the orthodontic jig packaging arrangement of FIG. 7a taken along site line 7b—7b therein;

FIG. 7c is a plan view of a portion of the jig packaging arrangement of FIG. 7a illustrating details of the manner in which a jig is securely maintained in position within a compartment in the packaging arrangement;

FIG. 7d is a sectional view of the packaging compartment and jig arrangement of FIG. 7c taking along site line 7d—7d therein;

FIG. 8 is a perspective view of an orthodontic jig in accordance with still another embodiment of the present invention, where the jig is provided with a handle for grasping and manipulating the jig;

FIG. 9 is a perspective view illustrating a jig and orthodontic bracket combination disposed on a highly angulated tooth, where the surfaces of the jig are aligned with the occlusal edges of the tooth;

DETAILED DESCRIPTION OF THE PREFERRED EMBODIMENTS

Figure 1:
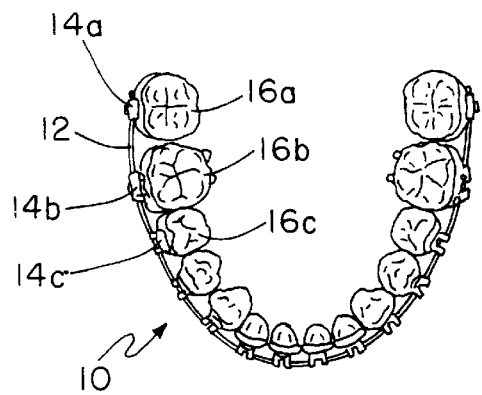
FIG. 1 is a schematic plan view illustrating the disposition of a conventional brace arrangement on a patient's teeth.

Referring to FIG. 1, there is shown a schematic plan view illustrating the disposition of a conventional orthodontic brace arrangement 10 on a set of teeth in a patient's mouth. Three of the patient's teeth are designated as elements 16a, 16b and 16c, with numerical designations of the remaining teeth omitted for simplicity. The orthodontic brace arrangement 10 shown in FIG. 1 is conventional in design and configuration and includes a plurality of brackets each affixed to a respective one of the teeth. Thus, orthodontic brackets 14a, 14b and 14c are respectively attached to teeth 16a, 16b and 16c by means of a conventional adhesive (not shown for simplicity). All of the brackets are attached to and connected by an arch wire 12 which applies a force to each of the teeth for moving the teeth into a desired alignment and orientation. The arch wire 12 is disposed in an arched configuration having a progressive curvature when viewed on a plan basis as shown on FIG. 1 and having a linear configuration when viewed on an elevational basis. Each bracket includes a pad portion for affixing to a respective tooth and a support portion for attachment to the arch wire 12 as described below. The pad and support portions of each bracket are preferably comprised of a high strength, inert material such as stainless steel. An orthodontic jig, or fixture, in accordance with the present invention provides for optimum positioning of each bracket on a respective tooth for more precise alignment of the teeth when moved into position and reoriented by the arch wire 12 as described in detail below.

Figure 2:
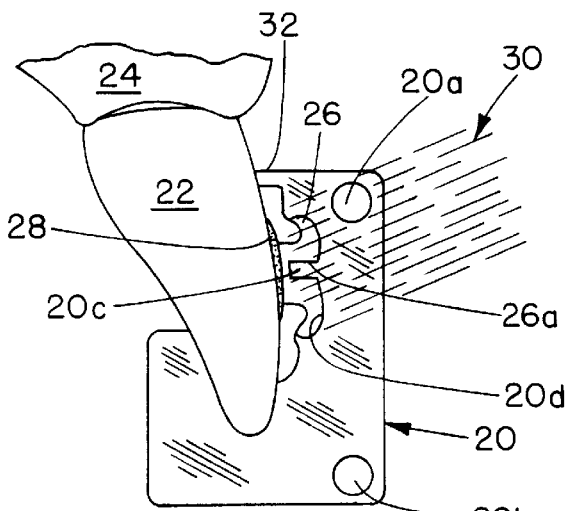
FIG. 2 is a side elevation view illustrating a jig and orthodontic bracket combination disposed on a tooth in accordance with one aspect of the present invention.

Referring to FIG. 2, there is shown a side elevation view of a jig 20 in accordance with one aspect of the present invention attached to a tooth 22 extending from a patient's gum 24. Jig 20 includes a housing having a cut-out inner portion in facing relation to tooth 22 which is adapted to receive the tooth as well as an orthodontic bracket 26 for attachment to a lateral surface of the tooth by means of a conventional adhesive 28. The pad portion of orthodontic bracket 26 engages the adhesive deposit 28 for securely attaching the bracket to tooth 22. An outer portion of the orthodontic bracket 26 includes a slot 26a therein. The cut-out portion of jig 20 includes a finger 20c adapted for insertion in the bracket's slot 26a for securely coupling the bracket to the jig during attachment of the bracket to tooth 22. The cut-out portion of the jig 20 includes a contoured surface 20d which is configured and sized so as to receive the outer surface of the orthodontic bracket 26 in a tight-fitting manner. The combination of the orthodontic bracket 26 and jig 20 are inserted over tooth 22 and the bracket becomes affixed to the tooth's lateral surface by means of adhesive 28. Jig 20 is then removed from tooth 22, with the bracket 26 securely maintained in fixed position on the tooth 22 by means of the adhesive 28. The bracket's slot 26a is adapted to receive the aforementioned arch wire in a conventional manner. The cutout inner portion of jig 20 is formed by means of CAD/CAM techniques as described below for optimum positioning of the orthodontic bracket 26 on the tooth 22 for aligning and orienting the tooth relative to the patient's other teeth in a desired manner.

In accordance with one aspect of the present invention, jig 20 is preferably comprised of a translucent material such as clear plastic. This permits a light sensitive adhesive 28 to be used for bonding orthodontic bracket 26 to tooth 22. By directing a light beam 30 such as in the visible blue spectrum through translucent jig 20 and onto the deposit of adhesive 28, the adhesive may be quickly cured for bonding the orthodontic bracket 26 to tooth 22. In addition to being translucent for use with light sensitive adhesives, jig 20 may also be provided with various color coded schemes to facilitate the use and installation of the jig on a designated tooth. For example, jig 20 may be provided with a first color-coded portion 20a of a first color and a second color coded portion 20b having a second color. As an example, the first color coded portion 20a may be used to designated the arch, either upper or lower, with which the jig 20 is to be used. Similarly, the second color coded portion 20b may be used to identify the quadrant within the designated arch with which the jig is intended for use. Finally, the entire body of jig 20 may be color-coded to indicate the specific tooth with which the jig is to be used. The color density of the jig 20 in the latter case would not be sufficient to attenuate light transmitted through the jig for the purpose of curing adhesive 28.

Jig 20 is preferably comprised of a somewhat flexible, resilient material to permit the jig to securely receive the orthodontic bracket 26 in a snap-acting manner and to be inserted on tooth 22 in a tight-fitting manner. This permits the jig 20 to securely engage the orthodontic bracket 26, while allowing the jig to be removed from the bracket and tooth 22 with the application of a predetermined amount of force. Jig 20 may further be provided with a standoff finger, or projection, 32 extending from an upper portion of the jig and engaging a lateral portion of tooth 22. Standoff finger 32 ensures the correct in/out or prominence registration of the jig from the tooth's lateral surface. The distal end of standoff projection 32 contacts the enamel portion of tooth 22 between bracket 26 and the incisal edge of the tooth and stabilizes the jig in position on the tooth. The dimensions of standoff projection 32 as well as the inner dimensions and configuration of jig 20 are derived from digital data via CAD/CAM techniques as described below. Jig 20 is preferably machined from a material that will not molecularly bond or crosslink with adhesive 28 so as to preclude accidental adherence of the adhesive to the jig. Such non-bonding plastics used for jig 20 include polyethylene, polypropylene and other waxy olefins.

Figure 3A:
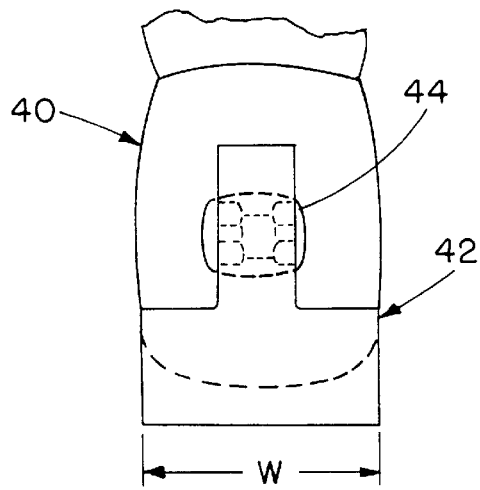
FIGS. 3a and 3b are side elevation views illustrating a jig in accordance with the present invention for positioning an orthodontic bracket on a tooth, where the jig is respectively shown having essentially the same width as the tooth and having a reduced width on the order of the width of the orthodontic bracket.
Figure 3B:
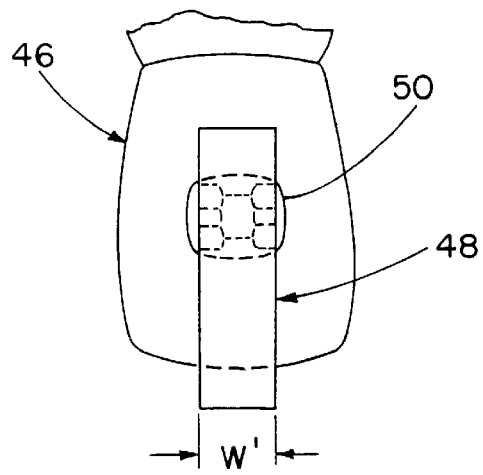

Referring to FIGS. 3*a* and 3*b*, there are shown two versions of a jig for attaching an orthodontic bracket to a tooth in accordance with another aspect of the present invention. In FIG. 3*a*, jig 42 is used for attaching orthodontic bracket 44 to a labial surface of a tooth 40 which is generally devoid of any distinguishing anatomy. In this case, the distal portion of jig 42 is provided with a width W which is substantially of the same width as tooth 40. Extending the width of jig 42 to be substantially the same as the width of tooth 40 permits the jig to engage the mesial and distal edges of the tooth to permit the jig to "lock" onto a tooth lacking any distinguishing anatomy or surface characteristics. In FIG. 3*b*, jig 48 is shown having a width W' which is substantially of the same width as bracket 50 which is affixed to tooth 46. In some cases, it may be desirable to provide a jig having the same width as the bracket with which the jig is used.

Figure 4A:
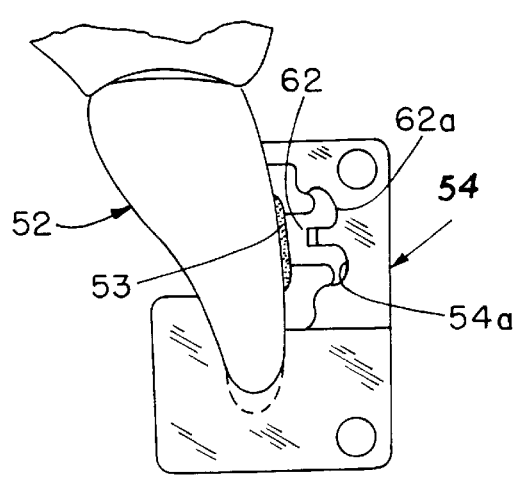
FIGS. 4a and 4b are side elevation views showing the combination of an orthodontic bracket and jig in accordance with another aspect of the present invention attached to a patient's tooth, where the orthodontic bracket and connecting portion of the jig have different shapes and configurations in the two figures.
Figure 4B:
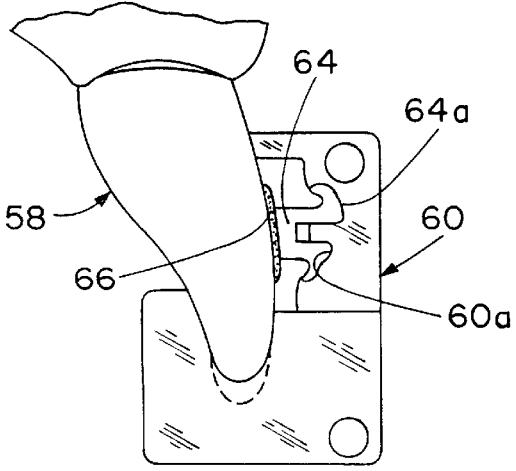

Referring to FIGS. 4*a* and 4*b*, there is shown a side elevation view of two versions of a jig in accordance with the present invention used in combination with two orthodontic brackets having different configurations and dimensions. Thus, in FIG. 4*a*, jig 54 is shown having an inner contoured surface 54*a* which matches the contour of the surface 62*a* of orthodontic bracket 62. Jig 54 is used for securely attaching orthodontic bracket 62 to tooth 52 by means of an adhesive deposit 53. Similarly, referring to FIG. 4*b*, jig 60 is shown having an inner contoured surface 60*a* which is sized and shaped to match the contoured outer surface 64*a* of orthodontic bracket 64. Jig 60 is used for securely attaching orthodontic bracket 64 to tooth 58 by means of an adhesive deposit 66. As shown in FIGS. 4*a* and 4*b*, orthodontic brackets 62 and 64 are non-standard in shape and possess different configured and dimensioned contoured outer surfaces. Thus, a jig in accordance with the present invention may be used with an orthodontic bracket having virtually any configuration and size. This feature permits an orthodontist to use a jig in accordance with the present invention with the orthodontic bracket system with which the orthodontist is familiar without requiring the orthodontist to change to another bracket system.

Referring to FIG. 5, there is shown a side elevation view of another embodiment of a jig 72 for affixing an orthodontic bracket 74 to a tooth 70 in accordance with the present invention. A perspective view of the inventive jig 72 is shown in FIG. 6. Jig 72 includes a cut-out, or recessed, portion 72*a* for receiving and engaging a tooth 70. Jig 72 further includes upper and lower recessed portions 72*b* and 72*c* for receiving an orthodontic bracket 74. Jig 72 maintains orthodontic bracket 74 in a fixed position relative to tooth 70 for attaching the bracket to the tooth by means of an adhesive 76 as previously described. Jig 72 is further provided with a standoff projection 78 for stabilizing the jig on tooth 70 and ensuring exact in/out, or prominence, registration of jig from the lateral surface of the tooth. A finger 82 extends from the jig's inner surface between the upper and lower recesses 72*b*, 72*c*. Jig finger 82 is adapted for insertion in a slot 74*a* within the orthodontic bracket 74. The upper and lower recessed portions 72*b*, 72*c* and the intermediate finger 82 within jig 72 ensure secure coupling of the jig to the orthodontic bracket 74. Disposed within the upper and lower recesses 72*b*, 72*c* are upper and lower positioning stops 80*a* and 80*b*, respectively. Upper and lower recessed portions 72*b*, 72*c* allow jig 72 to engage the orthodontic bracket 74 in a sliding manner. With respective upper and lower portions of orthodontic bracket 74 securely disposed with an upper and lower recessed portions 72*b*, 72*c* of jig 72, the orthodontic bracket may be securely attached to tooth 70 as previously described. Positioning stops 80*a* and 80*b* ensure that the orthodontic bracket 74 is precisely positioned within the jig and restrict relative movement between the bracket and jig in the mesial-distal direction. Following bonding of the orthodontic bracket 76 to tooth 70 by means of adhesive 76, jig 72 may be removed from the bracket in a sliding manner via the open ends of the upper and lower recessed portions 72*b* and 72*c* of the jig.

Referring to FIG. 7*a*, there is shown a plan view of a jig packaging arrangement 90 in accordance with another aspect of the present invention. A sectional view of the jig packaging arrangement 90 of FIG. 7*a* taken along site line 7*b*–7*d* therein is shown in FIG. 7*b*. The jig packaging arrangement 90 includes a backing sheet 92 which is preferably opaque and comprised of a semi-rigid, opaque material such as reinforced paper or cardboard. Attached to a surface of backing sheet 92 is a cover sheet 94 which includes a plurality of spaced upraised compartments, three of which are identified as elements 100*a*, 100*b* and 100*c*. Each of the upraised compartments is adapted to receive and enclose the combination of a jig and positioning brace as shown for the combinations of jig 96 and positioning brace 98 in upraised compartment 100*a* and jig 102 and positioning brace 104 in upraised compartment 100*d*. A jig and positioning brace combination is not shown in the remaining upraised portions illustrated in FIGS. 7*a* and 7*b* for the sake of simplicity.

With reference to the plan view of FIG. 7*c* and the sectional view of FIG. 7*d*, which is taken along site line 7*d*—7*d* in FIG. 7*c*, additional details of the jig packaging arrangement will now be described. The combination of backing sheet 92 and cover sheet 94 is commonly referred to as a "blister" packaging arrangement and is well known in the packaging art. Each compartment 110 has disposed thereabout a peripheral lip or ledge 110*a*. Each orthodontic bracket 112 is attached to a respective positioning brace 114 by conventional means such as an adhesive 120 or by connecting tabs or in a snap-acting manner, as described below. The positioning brace 114 is generally "H"-shaped, although it is not limited to this particular configuration, and lies flat on the backing sheet 118 when positioned within the upraised compartment 110 and attached to jig 112. With jig 112 securely attached to positioning brace 114 and the outer edges of the positioning brace disposed beneath and engaging the peripheral lip 110*a* of the upraised compartment 110, the combination of the positioning brace and jig are maintained in fixed position within the compartment. An adhesive deposit 121 may be affixed to jig 112 for attaching the jig to a tooth. Where the adhesive is of the light curing type, the cover sheet 116 should also be opaque. Otherwise, the cover sheet 116 may be comprised of clear plastic as in a common form of blister packaging.

Referring to FIG. 8, there is shown a perspective view of yet another embodiment of a jig 130 in accordance with the present invention. Jig 130 includes a tooth and orthodontic bracket engaging portion 132 as previously described. Jig 130 further includes a handle 134 attached to and extending from the tooth and orthodontic bracket engaging portion 132 thereof. Handle 134 facilitates manual manipulation of the jig 130 such as during installation on and removal from a tooth. Handle 134 may include an elongated aperture 136 therein to facilitate grasping by one's fingers or by a tool such as tweezers or another instrument during installation and removal of jig 130. The tooth and orthodontic bracket engaging portion 132 and handle 134 of jig 130 are preferably integral with one another and are formed from a common piece.

Referring to FIG. 9, there is shown a perspective view of a combination of a jig 140 for affixing an orthodontic bracket 146 to a tooth 142 having a highly angulated shape in accordance with yet another aspect of the present invention. Tooth 142 is disposed in and extends from a patient's gum 144. Jig 140 includes mesial and distal edges 140a and 140b respectively aligned with the mesial and distal lateral surfaces of the crown of tooth 142. In addition, opposed lateral edges 140c and 140d of jig 140 are aligned with the central axis X–X' of the crown of tooth 142. In addition, the distal edge 140e of jig 140 is aligned with the occlusal edge 142a (shown in dotted line form) of tooth 142. Jig 140 of FIG. 9 facilitates visual confirmation that it is in the correct position on tooth 142 by the alignment of the jig's mesial and distal edges with those edges of its associated tooth, alignment of its lateral edges with the tooth's central axis, and alignment of its distal edge with the occlusal edge of its associated tooth, which alignments can be easily checked visually. Visual confirmation of alignment of the jig with its associated tooth is particularly important in the case of highly angulated teeth.

Figure 10:
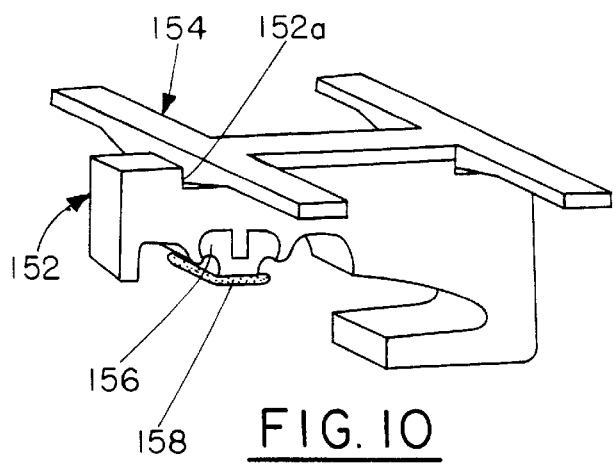
FIG. 10 is a perspective view of a jig and positioning brace combination for use in the jig packaging arrangement of FIGS. 7a–7d.

Referring to FIG. 10, there is shown another mounting arrangement for attaching a jig 152 to a positioning brace 154 for use in the packaging arrangement previously described. Prior to packaging, an orthodontic bracket 156 to which is applied an adhesive pad 158 may be attached to jig 152 as previously described. Jig 152 may be provided with a slot 152a in a lateral surface thereof for receiving the positioning brace 154 in a snap-acting manner. Positioning brace 154 engages the packaging cover sheet as previously described for maintaining jig 152 in fixed position within a compartment in the packaging arrangement. By maintaining jig 152 in a fixed position within a respective packaging compartment, the adhesive pad 158 disposed on the orthodontic bracket 156 is maintained in spaced relation from the sheets forming the compartment within which the jig is disposed. This permits a combination of jig 152, orthodontic bracket 156 and adhesive pad 158 to be directly affixed to a tooth following its removal from a packaging compartment and separation of the positioning brace 154 from the jig. Positioning brace 154 is preferably comprised of plastic and may be formed from the same piece of material as jig 152 itself as previously described.

Figure 11:
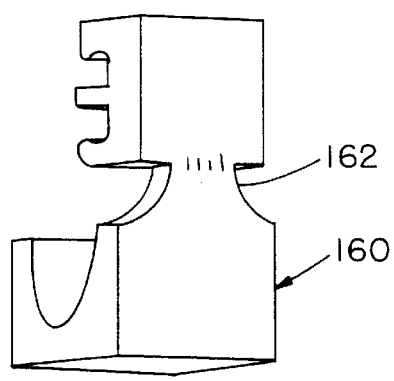
FIG. 11 is a perspective view of an orthodontic jig in accordance with yet another aspect of the present invention.

Referring to FIG. 11, there is shown another embodiment of a jig 160 in accordance with the present invention. Jig 160 includes a narrow portion 162 forming a deformation zone in the jig. The narrow portion 162 allows for flexure of jig 160 during removal of the jig from its associated orthodontic bracket which is bonded to a tooth without patient discomfort or failure of not-fully cured adhesive bonding the bracket to the tooth. Following deformation of the jig 160 during removal in the area of its narrow portion 162, the jig assumes its original shape permitting the jig to be reused in the event that the bracket with which it is employed needs to be replaced on the same tooth.

Figure 12:
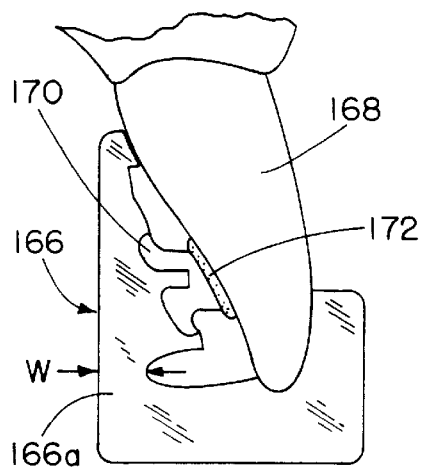
FIGS. 12 and 13 are side elevation views showing a jig and orthodontic bracket combination respectively attached to the inside surface and the outside surface of a tooth in accordance with another aspect of the present invention.
Figure 13:
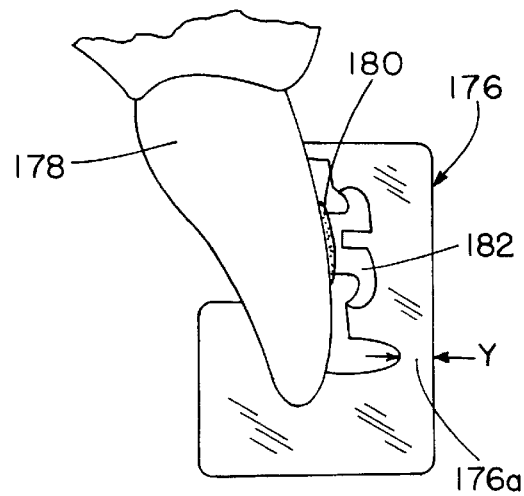

FIGS. 12 and 13 are side elevation views of another arrangement for a jig for attaching an orthodontic bracket to a tooth which facilitates removal of the jig following attachment of the bracket to the tooth. In FIG. 12, jig 166 is used for attaching an orthodontic bracket 170 to the inner surface of a tooth 168 by means of adhesive 172. Jig 166 includes a portion of reduced thickness 166a having a width W. Jig 166 is designed to flex or perhaps even fail along its reduced thickness portion 166a during removal of the jig from tooth 168 and orthodontic bracket 170. Elastic deformation or failure of jig 166 thus occurs over the reduced thickness portion 166a having thickness W of the jig to facilitate removal of the jig from tooth 168.

Referring to FIG. 13, there is shown a side elevation view of another arrangement of a jig 176 for attaching an orthodontic bracket 182 to the outer surface of a tooth 178 by means of adhesive 180. Jig 176 also includes a reduced thickness portion 176a having thickness Y of which is adapted for flexure or failure to facilitate removal of the jig from tooth 178 and orthodontic bracket 182 after the bracket is affixed to the tooth. Once severed, the two sections of the jig 176 may be removed from tooth 178 and orthodontic bracket 182.

Figure 14:
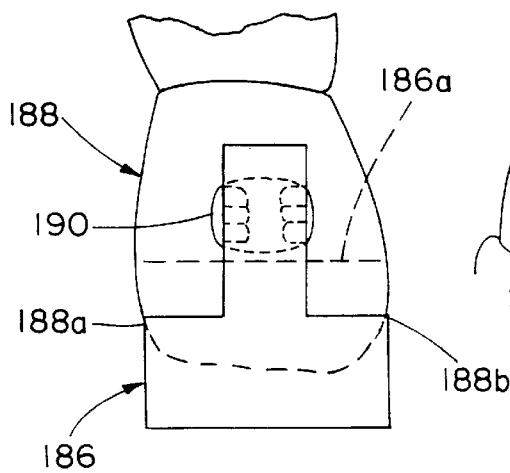
FIG. 14 is a side elevation view shown partially in phantom of a jig and orthodontic bracket combination attached to a tooth, where the jig engages the mesial and distal occlusal corners of the tooth in accordance with yet another aspect of the present invention.

Referring to FIG. 14, there is shown another embodiment of a jig 186 for affixing an orthodontic bracket 190 to the lateral surface of a tooth 188. In the embodiment of FIG. 14, jig 186 includes lateral edges for engaging the mesial and distal occlusal corners 188a and 188b of tooth 188. Jig 186 further includes a lingual edge 186a (shown in dotted line form) for engaging the lingual surface of tooth 188. By securely engaging the various aforementioned surfaces of tooth 188, jig 186 is positively locked in its intended position on the tooth for more accurate and secure positioning of orthodontic bracket 190 on the tooth.

Figure 15:
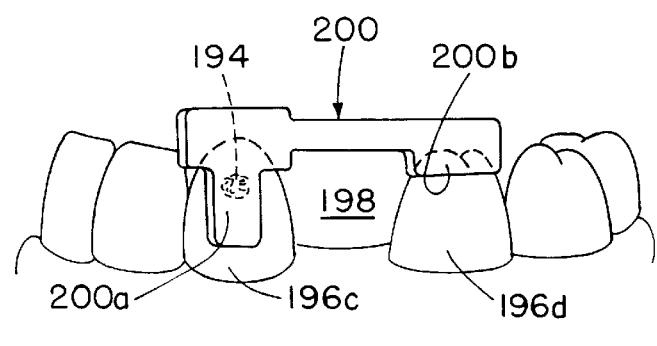
FIG. 15 is a perspective view shown partially in phantom of another embodiment of a jig in accordance with the present where the jig bridges a gap between two adjacent teeth.

Referring to FIG. 15, there is shown still another embodiment of a jig 200 for attaching an orthodontic bracket 194 (shown in dotted line form) to a tooth 196c. In the embodiment shown in FIG. 15, jig 200 spans and engages adjacent teeth 196c and 196d which are separated by a gap, or space, 198. Space 198 may be due to the extraction of a tooth or may be the site of a permanent tooth which has not yet appeared. Jig 200 includes first and second end portions 200a and 200b which are respectively adapted for securely engaging teeth 196c and 196d. Jig 200 is shaped for optimum positioning of orthodontic bracket 194 on tooth 196c, taking into consideration the maloccluding pretreatment positions of adjacent, separated teeth 196c and 196d. A jig 200 such as shown in FIG. 15 is particularly helpful for the reorientation of highly rotated teeth separated by a space or in any situation where it is likely that the jig will require additional stabilization to that available from engaging the target tooth alone.

There has thus been shown an orthodontic bracket placement jig and an installation method therefor. The placement jig is adapted for use with conventional, off-the-shelf orthodontic appliance brackets and arch wires for optimum positioning of a bracket on its associated tooth. Computer modeling of the patient's mouth and individual teeth employing digital scanning techniques allows each individual jig to be custom sized and shaped by CAD/CAM for precise positioning of the orthodontic bracket on each tooth for optimum re-positioning and re-orientation of the teeth. One embodiment of the jig is translucent to allow for the transmission of light for curing a light sensitive adhesive applied to the bracket for affixing the bracket to a tooth. The jig may also be provided with one or more color-coded indicia such as for designating the arch (upper or lower) and the particular tooth with which the jig is to be used. The jig may also be provided with elasticity to allow for deformation or failure of the jig to facilitate its removal from the tooth and may further include an integral occlusal standoff extension to ensure proper in/out, or prominence, registration from the tooth's enamel surface as well as an alignment tab to ensure proper positioning of the jig on its associated tooth. The width of the jig may vary from the width of the appliance to the full width of the tooth itself, where the tooth lacks distinguishing anatomy. A set of a jigs for a full set of teeth is packaged in a blister pack arrangement, with each jig attached to an associated removable brace for secure, fixed positioning of a jig and bracket combination within an individual upraised compartment of the blister pack. The top sheet forming the individual compartments in the packaging arrangement may be either clear (transparent) or opaque where a light sensitive adhesive is affixed to the orthodontic bracket. Another embodiment of the jig spans a gap or space between adjacent teeth for positioning of an orthodontic bracket on one of the teeth where the required stabilization of the jig during attachment of the bracket to the tooth cannot be achieved by engaging the target tooth alone.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

I claim:

1. Apparatus for attaching an orthodontic bracket to a tooth of a patient by means of an adhesive, said apparatus comprising:

a housing;

a first recessed portion of said housing for receiving and engaging the tooth in a tight-fitting manner;

a second recessed portion of said housing for receiving and engaging the orthodontic bracket and for securely maintaining the orthodontic bracket in contact with an adhesive on a lateral surface of the tooth; and a standoff projection attached to and extending from said housing for engaging the tooth and providing a predetermined stand-off spacing between the housing and the surface of the tooth.

2. The apparatus of claim 1 wherein said housing has a width substantially equal to the mesial-distal width of said tooth for secure mounting of said housing on a tooth generally lacking a distinguishing anatomy.

3. The apparatus of claim 1 wherein said housing has a width substantially equal to the width of the orthodontic bracket.

4. The apparatus of claim 1 wherein said standoff projection engages the tooth intermediate the orthodontic bracket and an incisal edge of the tooth.

5. The apparatus of claim 1 wherein the adhesive is cured by light incident thereon and wherein said housing is translucent.

6. The apparatus of claim 5 wherein the adhesive is responsive to blue light transmitted through said housing and incident upon the adhesive for the curing thereof.

7. The apparatus of claim 1 further comprising a handle coupled to said housing to facilitate the manipulation of the housing during installation on and removal from a tooth.

8. The apparatus of claim 7 wherein said handle includes an aperture therein.

9. The apparatus of claim 1 wherein said housing includes a weakened portion capable of deforming or breaking under stress to facilitate removal of the housing from a tooth after attaching an orthodontic bracket to the tooth.

10. The apparatus of claim 9 wherein said weakened portion is characterized as having a reduced thickness.

11. The apparatus of claim 1 wherein said first recessed portion includes mesial, distal and lingual portions for engaging the tooth's mesial and distal occlusal corners and a lingual surface of the tooth.

12. The apparatus of claim 1 wherein said housing further includes a third recessed portion for engaging a second adjacent tooth, wherein a gap is disposed intermediate the teeth and said housing is stabilized for more securely attaching the housing to the first tooth.

13. The apparatus of claim 1 further comprising color-coded means disposed on said housing for indicating the location of the patient's mouth where the apparatus is to be installed.

14. The apparatus of claim 13 wherein said color-coded means indicates the arch in which the apparatus is intended for use, the portion of said arch in which the apparatus is intended for use, and the tooth with which the apparatus is intended for use.

15. The apparatus of claim 13 wherein said color-coded means comprises the color of said housing.

16. The apparatus of claim 15 wherein said color-coded means further includes one or more designated portions on the surface of said housing each having a respective color.

17. Apparatus for attaching an orthodontic bracket to a tooth of a patient by means of an adhesive, said apparatus comprising:

a housing;

a first recessed portion of said housing for receiving and engaging the tooth in a tight-fitting manner;

a second recessed portion of said housing for receiving and engaging a distal surface portion of the orthodontic bracket and for securely maintaining the orthodontic bracket in contact with an adhesive on a lateral surface of the tooth; and positioning stop means in said second recessed portion for engaging the orthodontic bracket when the orthodontic bracket is in contact with said adhesive on a lateral surface of the tooth and ensuring proper positioning of the orthodontic bracket in said housing, wherein said positioning stop means restricts mesial-distal movement between the orthodontic bracket and said housing.

* * * * *